United States Patent [19]

Mete et al.

[11] Patent Number: 5,225,423
[45] Date of Patent: Jul. 6, 1993

[54] BUTENONE COMPOUNDS, THEIR PREPARATION AND THEIR USE AS PESTICIDES

[75] Inventors: Antonio Mete, Gillingham; Lai C. Chan, Liverpool, both of England

[73] Assignee: Shell Research Limited, United Kingdom

[21] Appl. No.: 591,767

[22] Filed: Oct. 2, 1990

[30] Foreign Application Priority Data

Oct. 27, 1989 [GB] United Kingdom ............... 8924280

[51] Int. Cl.$^5$ ................. C07D 213/42; C07D 213/52; A01N 43/40
[52] U.S. Cl. .................................. 514/357; 514/352; 546/305; 546/331; 546/334
[58] Field of Search ............... 546/286, 287, 288, 289, 546/295, 296, 297, 298, 299, 300, 312, 306, 307, 310, 314, 315, 332, 334, 291, 292, 305, 326, 331, 332, 334; 514/344, 348, 349, 350, 351, 352, 353, 354, 355, 356, 357, 345

[56] References Cited

FOREIGN PATENT DOCUMENTS 302389 2/1989 European Pat. Off. ............ 546/304
302833 2/1989 European Pat. Off. ............ 546/304
3639877 5/1988 Fed. Rep. of Germany ...... 546/304

Primary Examiner—C. Warren Ivy
Assistant Examiner—Phyllis Spivack

[57] ABSTRACT

A butenone compound having the general formula I:

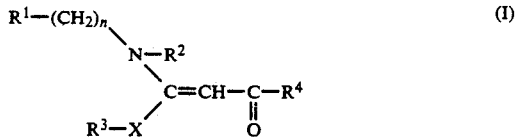

wherein $R^1$ represents a pyridyl or thiazolyl group bearing one or more substituents independantly selected from halogen atoms, alkyl, alkoxy, alkylthio, haloalkyl, cyano, alkoxycarbonyl, alkylamino and dialkylamino; $R^2$ represents a hydrogen atom, an alkyl group or an alkylcarbonyl group; $R^3$ represents an alkyl group; $R^4$ represents a haloalkyl group; X represents a sulphur atom or a group of formula $N-R^5$, wherein $R^5$ represents a hydrogen atom, an alkyl group or an alkylcarbonyl group; and n is 0 or 1, methods for their preparation and their use in combating pests.

13 Claims, No Drawings

BUTENONE COMPOUNDS, THEIR PREPARATION AND THEIR USE AS PESTICIDES

The present invention relates to butenone compounds, to processes for their preparation and to the use of such compounds as pesticides.

European Patent Application publication No. EP 0 302 389 (EP-A-0 302 389) discloses insecticidal/pesticidal compositions comprising an α-unsaturated amine of the general formula:

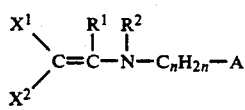

wherein $X^1$ and $X^2$ are such that one is an electron-attracting group with the other being a hydrogen atom or an electron-attracting group; $R^1$ is a group attached through a carbon, oxygen, sulphur or nitrogen atom; $R^2$ is a hydrogen atom or a group attached through a carbon, nitrogen or oxygen atom; n is an integer equal to 0, 1 or 2; and A is a heterocyclic group or a cyclic hydrocarbon group; or a salt thereof.

$R^1$ is disclosed as preferably being a group attached through a nitrogen atom and includes an amino group optionally substituted, for example, by one or more groups selected from alkyl, aryl, aralkyl, heterocyclic, acyl, alkoxycarbonyl, aryloxycarbonyl, heterocycleoxycarbonyl, arylsulphonyl, alkylsulphonyl, dialkoxyphosphoryl, cycloalkyl, alkenyl, cycloalkenyl and alkynyl.

$R^2$ may be a $C_{1-4}$ acyl, alkyl, alkenyl, cycloalkyl, $C_{6-10}$ aryl, $C_{7-9}$ aralkyl or a heterocyclic group, an amino group as mentioned above with reference to $R^1$, or an alkoxy, cycloalkoxy, alkenyloxy, cycloalkenyloxy, $C_{6-18}$ aryloxy, heterocycleoxy or hydroxy group.

Heterocyclic groups represented by $R^1$ and $R^2$ as mentioned above and represented by A include, among others, 5- to 8- membered rings each containing 1 to 5 hetero atoms such as oxygen, sulphur and nitrogen or fused rings derived therefrom.

The electron-attracting groups represented by $X^1$ and $X^2$ in the above formula are said to include, among others, cyano, nitro, $C_{1-4}$ alkoxycarbonyl (e.g. methoxycarbonyl, ethoxycarbonyl, etc.), heterocycleoxycarbonyl (e.g. pyridyloxycarbonyl, thienyloxycarbonyl, etc.), $C_{1-4}$ alkylsulphonyl which may be substituted with halogen (e.g. methylsulphonyl, trifluoromethylsulphonyl, ethylsulphonyl, etc.), aminosulphonyl, di-$C_{1-4}$ alkoxyphosphoryl (e.g. diethoxyphosphoryl, etc.), $C_{1-4}$ aryl which may be substituted with halogen (e.g. a $C_{1-4}$ alkylcarbonyl such as acetyl, trichloroacetyl, trifluoroacetyl, etc.), $C_{1-4}$ alkylsulphonylthiocarbamoyl (e.g. methylsulphonylthiocarbamoyl, etc.) carbamoyl and so on. One of $X^1$ and $X^2$ may be a halogen atom such as fluorine, chlorine, bromine or iodine, and $X^1$ and $X^2$ may join together with the adjacent carbon atom to form a ring.

Preferred examples of the group

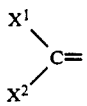

in the above general formula are stated in EP-A-0 302 389 to be $O_2NCH=$. Indeed, EP-A-0 302 389 is most particularly directed to compounds in which one of $X^1$ and $X^2$ is the group $NO_2$, with all of the compounds exemplified in the specification being nitroethylene compounds.

A broad range of the nitroethylene compounds exemplified in EP-A-0 302 389 are demonstrated in the specification as exhibiting insecticidal activity against the brown planthopper (Nilaparvata luqens).

However, contrary to the teaching of EP-A-0 302 389, it has been found that a range of compounds embraced by the disclosure of the specification of EP-A-0 302 389 exhibit only a very low level of activity or are inactive as insecticides. In particular, it has been found that, unlike the broad range of nitroethylene compounds exemplified in the specification, a number of analogous compounds in which one of $X^1$ and $X^2$ is an acetyl group bearing a halogen substituent are either inactive or exhibit only a low level of activity against a range of insects, including the brown planthopper.

In addition, it has been found that nitroethylene compounds of the type exemplified in EP-A-0 302 389 possess only low levels of thermal and photolytic stability. Pesticidally active compounds having such levels of thermal stability may be precluded from use in applications in which they are exposed to heat. Such compounds are particularly vulnerable to degradation in hot climates. Indeed, it has been found that certain of the nitroethylene compounds exemplified in EP-A-0 302 389 possess the undesirable property of decomposing exothermally. A compound possessing only a low level of photolytic stability, whilst possibly exhibiting a high initial level of insecticidal activity, is rapidly rendered inactive after application to a locus upon exposure to light.

West German Offenlegungsschrift 36 39 877 (DE-A-36 39 877) discloses compounds having the general formula:

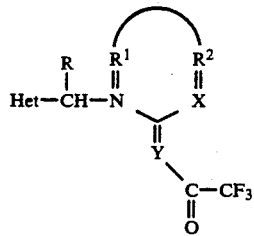

in which Het represents one or more substituted heteroaryl groups; R represents an oxygen, sulphur or nitrogen atom or the group NH or —$CR^4$, in which $R^4$ represents a hydrogen atom or an alkyl group; Y represents a nitrogen atom or the group —$CR^3$, in which $R^3$ represents a hydrogen atom or the group —CO—$CF_3$; and $R^1$ and $R^2$ together with the adjacent nitrogen atom and the moiety X represent certain heterocyclic groups containing one or more heteroatoms independently selected from nitrogen, oxygen and sulphur. The compounds are disclosed as being of use as insecticides and ectoparasiticides. No mention is made in the specification of DE-A-36 39 877 as to the level of thermal or photolytic stability exhibited by the compounds disclosed therein.

Most surprisingly, it has now been discovered that a select range of compounds embraced by the general disclosure of EP-A-0 302 389, but not specifically exemplified or disclosed therein, having the above general formula A in which one of $X^1$ or $X^2$ is an acetyl group bearing a halogen substituent exhibit a significant level of insecticidal activity and possess an unexpectedly high level of both thermal and photolytic stability compared to the analogous nitroethylene compounds.

Accordingly, the present invention provides a butenone compound having the general formula I:

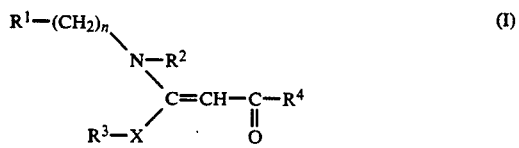

wherein
- $R^1$ represents a pyridyl or thiazolyl group bearing one or more substituents independently selected from halogen atoms, alkyl, alkoxy, alkylthio, haloalkyl, cyano, alkoxycarbonyl, alkylamino and dialkylamino;
- $R^2$ represents a hydrogen atom, an alkyl group or an alkylcarbonyl group;
- $R^3$ represents an alkyl group;
- $R^4$ represents a haloalkyl group;
- X represents a sulphur atom or a group of formula $N-R^5$, wherein $R^5$ represents a hydrogen atom, an alkyl group or an alkylcarbonyl group; and
- n is 0 or 1.

Alkyl moieties present in the compound of formula I may be straight chain or branched.

Any alkyl moiety present in the substituent in the group represented by $R^1$ is preferably $C_{1-6}$ alkyl, more preferably $C_{1-4}$ alkyl, especially methyl or ethyl. The group represented by $R^1$, however, preferably bears one or more halogen atoms as substituents, most preferably chlorine or bromine, especially chlorine. $R^1$ preferably represents a pyridyl group, most preferably a 3-pyridyl group. When $R^1$ represents a 3-pyridyl group it is preferably substituted at the 6-position by a chlorine or bromine atom. When $R^1$ represents a thiazolyl group it is preferably substituted at the 2-position by a chlorine or bromine atom. $R^1$ is most preferably a 6-chloro-3-pyridyl group.

Alkyl moieties present in the group represented $R^2$ are each preferably $C_{1-6}$ alkyl, more preferably $C_{1-4}$ alkyl, especially methyl or ethyl. Alkylcarbonyl groups represented by $R^2$ preferably bear one or more halogen atoms as substituents, preferred alkylcarbonyl groups being trihalomethylcarbonyl groups. Preferred compounds are those in which $R^2$ represents either a hydrogen atom, a methyl group or a trifluoromethylcarbonyl group.

Alkyl moieties present in the groups represented by $R^3$ are each preferably $C_{1-6}$ alkyl, more preferably $C_{1-4}$ alkyl, especially methyl or ethyl. Alkoxycarbonyl group represented by $R^3$ may bear one or more halogen atoms as substituents, trihalomethylcarbonyl groups being examples of suitable alkoxycarbonyl groups. Preferred compounds are those in which $R^3$ is a methyl group.

X represents a sulphur atom or, more preferably, a group of formula $N-R^5$. The alkyl group represented by $R^5$ is preferably $C_{1-6}$ alkyl, more preferably $C_{1-4}$ alkyl, especially methyl or ethyl. $R^5$ preferably represents a hydrogen atom or a methyl group.

Preferred compounds are those in which $R^3$ represents a methyl group and X represents the group $N-R^5$ in which $R^5$ represents a hydrogen atom or a methyl group.

The haloalkyl group represented by $R^4$ is preferably $C_{1-6}$ haloalkyl, more preferably $C_{1-4}$ haloalkyl, especially a halomethyl or haloethyl group. $R^4$ preferably represents a halomethyl group, more preferably a trihalomethyl group. Preferred compounds are those in which $R^4$ represents trichloromethyl and trifluoromethyl, compounds in which $R^4$ is trifluoromethyl being especially preferred.

Preferred compounds are those in which n is 1.

Those skilled in the art will appreciate that compounds having the general formula I above may exist as isomers (cis- and trans- isomers) and tautomers. All such isomers and tautomers and their mixtures are embraced by the present invention.

According to a further aspect of the present invention there is provided a process for the preparation of a compound having the general formula I as herein before defined, which process comprises reacting a compound having the general formula II:

wherein $R^1$, $R^2$ and n are as hereinbefore defined with a compound having the general formula III:

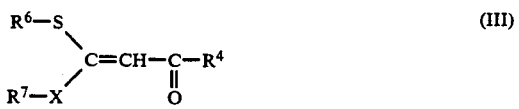

wherein $R^6$ represents an alkyl group; $R^7$ represents an alkyl group; and $R^4$ and X are as hereinbefore defined to yield a butenone compound having the general formula I in which $R^3$ is $R^7$, followed, when the desired product is a compound of formula I in which X is $N-R^5$ and X in the compound of formula III is a sulphur atom, by reacting the compound having the general formula I so obtained with an amine of formula $R^3R^5NH$ wherein $R^3$ and $R^5$ are as hereinbefore defined, to yield a compound having the general formula I in which X is $N-R^5$.

Reaction of the compound of formula II with the compound of formula III may conveniently be effected in the presence of an inert organic solvent. Suitable solvents include toluene, tetrahydrofuran, ethers, for example diethylether, alcohols, for example ethanol and isopropylalcohol, and other polar solvents, for example dimethylformamide, dimethylacetamide, N-methylpyrrolidine, dimethylsulphoxide and acetonitrile. The reaction may conveniently be effected at a temperature in the range of from 0° C. to the reflux temperature of the reaction mixture, very conveniently at the reflux temperature.

The compound of general formula III in which $R^6$ and $R^7$ are both methyl, $R^4$ is trifluoromethyl and X is a sulphur atom, namely 1,1-bismethylthio-4,4,4-trifluoro-1-buten-3-one, is known and is described in the published specification of German Patent Application No.

36 39 877 (DE-A-36 39 877). Other compounds of general formula III in which X is a sulphur atom may be prepared by a process analogous to that described in DE-A-36 39 877, namely the reaction of a compound having the general formula IV:

$$CH_3-\underset{\underset{O}{\|}}{C}-R^4 \qquad (IV)$$

wherein $R^4$ is as hereinbefore defined with carbon disulphide in the presence of a strong base, followed by reaction of the product so obtained with a compound of formula RL in which R is as hereinbefore defined and L is a leaving group. The process is conveniently effected in the presence of an aprotic organic solvent, for example dimethylformamide, dimethylsulphoxide or tetrahydrofuran. The process may be effected at a temperature in the range of from 0° to the reflux temperature of the reaction mixture, most conveniently room temperature. Suitable bases for use in the process include the alkali metal alkoxides, for example sodium ethoxide, alkali metal hydrides, for example sodium hydride and organic bases such as lithium diisopropylamide. Suitable leaving groups represented by L include halogen atoms, for example chlorine, bromine and iodine, and sulphate.

Compounds of general formula III in which X is $N-R^5$ may be prepared by reacting a compound of general formula III in which X is a sulphur atom with an amine of formula $R^3R^5NH$ wherein $R^3$ and $R^5$ are as hereinbefore defined. The reaction may conveniently be effected in the presence of an inert organic solvent. Examples of suitable solvents include toluene, tetrahydrofuran, ethers, such as diethylether, alcohols, such as ethanol and isopropylalcohol, and other polar solvents, for example dimethylformamide, dimethylacetamide, N-methylpyrrolidine, dimethylsulphoxide and acetonitrile. The reaction may conveniently be effected at a temperature in the range of from 0° C. to the reflux temperature of the reaction mixture, most conveniently at the reflux temperature.

The compounds of formula IV are haloacetones. Haloacetones are known materials or may be prepared by analogous methods to those used for preparing known haloacetones. Examples of commercially available haloacetones include 1,1,1-trifluoroacetone, for example ex Aldrich Chemie N.V., Brussels, Belgium.

The invention also provides a process for the preparation of a compound of formula I in which X represents a group of formula $N-R^5$, which process comprises reacting a compound having the general formula I in which X is a sulphur atom with an amine of formula $R^3R^5NH$ as herein before defined. The reaction may conveniently be effected in the presence of an inert solvent such as those listed above as suitable for the reaction of compounds of formula II with compounds of formula III, and at similar temperatures, namely at a temperature in the range of from 0° C. to the reflux temperature of the reaction mixture, most conveniently at the reflux temperature.

The compounds of formula II wherein $R^1$ is a substituted pyridyl group and n is 0 are aminopyridines. Substituted aminopyridines are known materials, or may be prepared by analogous methods to those used for preparing known aminopyridines. Examples of commercially available aminopyridines include 5-amino-2-chloropyridine (3-amino-6-chloropyridine) and 5-amino-2-methoxypyridine (3-amino-6-methoxypyridine), for example ex Aldrich Chemie N.V., Brussels, Belgium.

The compound of formula II in which $R^1$ is a substituted thiazolyl group are aminothiazoles. Substituted aminothiazoles are known materials, or may be prepared by analogous methods to those used for preparing known aminothiazoles as described in the art, for example Heterocyclic Compounds, Vol. 34 (part 2), pp 9 to 368 (John Wiley and Sons Inc. 1979).

Compounds of formula II wherein n is 1 and $R^2$ is a hydrogen atom may be prepared by reacting a phthalimide of formula V:

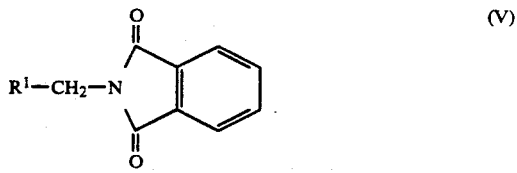

wherein $R^1$ is as hereinbefore defined with hydrazine, followed by treatment with an acid, conveniently hydrochloric acid. Reaction with hydrazine may conveniently be effected in an alcoholic medium, for example ethanol, conveniently at reflux temperature.

Compounds of formula V may be prepared by reacting the appropriate halomethyl derivative of formula VI:

$$R^1-CH_2-Hal \qquad (VI)$$

wherein $R^1$ is as hereinbefore defined and Hal is a halogen atom, preferably chlorine, with an alkali methal phthalimide, for example potassium phthalimide. The reaction may be effected without the presence of a solvent, and conveniently at a temperature in the range of from 150° C. to 170° C., for example about 160° C.

Compounds of formula II wherein n is 1 and $R^2$ is an alkyl group may be prepared by reacting an alkylamine with the appropriate halomethyl derivative of formula VI as defined above. The reaction may conveniently be effected in an alcoholic medium, for example ethanol, conveniently at reflux temperature.

Compounds of formula VI in which $R^1$ is a substituted pyridyl group may be prepared by halogenation of the corresponding compound of formula VII:

$$R^1-CH_2-OH \qquad (VII)$$

wherein $R^1$ is as hereinbefore defined. For example, compounds of formula VI in which Hal is a chlorine atom may conveniently be prepared by reaction of the appropriate compound of formula VII with thionylchloride, for example in a haloalkyl solvent such as chloroform, and at reflux temperature.

Compounds of formula VII in which $R^1$ is a pyridyl group are pyridylcarbinols. Some pyridylcarbinols are known, for example 3-pyridylcarbinol. In general pyridylcarbinols may be prepared from the appropriate pyridinecarboxylic acid by conversion of the acid to the acid chloride followed by reduction of the acid chloride. Optionally substituted pyridinecarboxylic acids are known materials, or may be prepared by analogous methods to those for preparing known pyridinecarboxylic acids. For example, nicotinic acid, 2-chloronicotinic acid, 6-chloronicotinic acid, and 5- bromonicotinic acid are commercially available, for example, ex Aldrich Chemie N.V., Brussels, Belgium.

Compounds of formula VI in which $R^1$ is a substituted thiazole group are halomethylthiazoles. Halomethylthiazoles are known materials, or may be prepared by analogous methods to those for preparing known halomethylthiazoles, as disclosed in Tetrahedron, (1981), 37, pages 2607 to 2611; J. Am. Chem. Soc, (1982), 104, pages 4461 to 4465; Zh. Obskch. Khim., (1962), 32 pages 570 to 575; Rev. Roumaine. Chim., (1965), 10, page 897 to 902 and as disclosed in German Offenlegungschrift DE 3,631,538.

The compounds of general formula I exhibit pesticidal, particularly insecticidal, activity. Accordingly the invention also provides a pesticidal composition comprising a carrier and, as active ingredient, a compound of general formula I.

The invention further provides a method of combating pests at a locus, which comprises treating the locus with a pesticidal compound or composition according to the invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites, and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts or polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing $\frac{1}{2}$–10% w of active ingredient. Granules are usually prepared to have a size between 10 and 100 BS mesh (1.676–0.152 mm), and may be manufactured by agglomeration or impregnation techniques. Generally, granules will contain $\frac{1}{2}$–75% w active ingredient and 0–10% w of additives such as stabilisers, surfactants, slow release modifiers and binding agents. The so-called "dry flowable powders" consist of relatively small granules having a relatively high concentration usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsion, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

Compositions in accordance with the invention may also contain other ingredients, for example other compounds possessing pesticidal, herbicidal, or fungicidal properties. The compounds of the invention may be found to be especially useful when applied in admixture with other insecticides and/or acaricides, e.g. organophosphates, pyrethroids, ureas and organotin compounds, for example the commercial products fenvalerate, permethrin, cypermethrin, deltamethrin, alphacypermethrin, fenbutatin oxide, flufenoxuron, diflubenzuron and trefluron.

The invention will be further understood from the following illustrative Examples, in which Examples 1 to 5 relate to the preparation of starting materials, Examples 6 to 14 relate to compounds of the invention and their preparation, Example 15 relates to pesticidal activity tests, Example 16 relates to thermal stability tests and Example 17 relates to photostability tests.

EXAMPLE 1

1,1-Bismethylthio-4,4,4-trifluoro-1-buten-3-one

Sodium hydride (50% dispersion in oil) (14.4 g, 0.3 mol) was suspended in dry N,N-dimethyl formamide (200 ml) and stirred under an atmosphere of dry nitrogen. The resulting suspension was then cooled using an ice-bath. A solution of carbon disulphide (31.7 g, 0.43 mol) and 1,1,1-trifluoroacetone (16.8 g, 0.15 mol) in N,N-dimethylformamide (50 ml) was added dropwise. When the addition had been completed, the resulting mixture was heated to 20° C. and maintained at that temperature with stirring for 1 hour. The resulting mixture was cooled using an ice-bath and methyliodide (25 ml) was added dropwise. The resulting mixture was heated to 20° C. and maintained at that temperature with stirring for 18 hours, after which the mixture was quenched with water (1000 ml) and extracted with ether (4×250 ml). The extracts were combined, washed with water (2×250 ml), washed with saturated brine (250 ml) and dried using magnesium sulphate. The solvent was removed by evaporation under reduced pressure to yield a dark brown solid. Recrystallization of the solid from ether/petrol gave 1,1-bismethylthio-4,4,4-trifluoro-1-buten-3-one, as a yellow crystalline product in a yield of 16.5 g (51%), melting point 97° C.

Analysis: Calculated: 33.3%C 3.3%H
Found: 33.2%C 3.0%H

EXAMPLE 2

1-Dimethylamino-1-methylthio-4,4,4-trifluoro-1-buten-3-one

The product of Example 1, 1,1-bismethylthio-4,4,4-trifluoro-1-buten-2-one, (2.16 g, 0.01 mol) and dimethylamine (0.45 g, 0.01 mol) were dissolved in ethanol (30 ml). The resulting solution was heated to 50° C. and maintained at that temperature with stirring for 1 hour. After this time, the resulting mixture was cooled to ambient temperature (20° C.) and the solvent was removed by evaporation under reduced pressure yielding a yellow residue. Chromatographic purifications of the solid using a silica column eluted with dichloromethane/methanol (30:1) gave the product, 1-dimethylamino-1-methylthio-4,4,4-trifluoro-1-buten-3-one, as a yellow oil in a yield of 2.1 g (98%).

NMR (CDCl), delta (ppm): 2.47 (s,3H), 3.26 (s,6H), 5.20 (s,1H)

EXAMPLE 3

N-(2-chloro-5-thiazolylmethyl)-N-methylamine

2-Chloro-5-thiazolylmethylchloride (5.0 g, 0.03 mol) and methylamine (4.6 g, 0.15 mol) were dissolved in ethanol (50 ml). The resulting solution was heated under reflux for 2 hours. The resulting mixture was allowed to cool to ambient temperature (20° C.) and the solvent was removed by evaporation under reduced pressure. The residue was added to a mixture of dichloromethane (150 ml) and aqueous sodium hydroxide (2N, 50 ml) and the mixture agitated. The two phases were allowed to separate and the aqueous phase was removed. Further aqueous sodium hydroxide (2N, 50 ml) was added to the organic phase and the step repeated. The aqueous phases were combined and washed with dichloromethane (50 ml). The dichloromethane product so obtained was combined with the original organic phase, washed with saturated brine (100 ml) and dried using magnesium sulphate. The solvent was evaporated to give N-(2-chloro-5-thiazolylmethyl)-N-methylamine as a yellow oil in a yield of 3.55 g (73%).

NMR (CDCl$_3$), delta (ppm):1.30 (broad,1H), 2.39 (s,3H) 3.84 (s,2H), 7.30 (s,1H)

EXAMPLE 4

6-chloro-3-pyridylmethylamine (a) Preparation of 2-chloro-5-hydroxymethylpyridine 6-Chloronicotinic acid (23.36 g, 0.18 mol), phosphorus pentachloride (41.65 g, 0.20 mol) and phosphorus oxychloride (20.50 ml, 0.22 mol) were stirred vigorously together at ambient temperature (20° C.). The resulting mixture was heated with stirring to 120° C. and kept at that temperature for a further 3 hours. The mixture was then allowed to cool to ambient temperature (20° C.) and excess phosphorus oxychloride was evaporated off under reduced pressure to yield 6-chloronicotinyl chloride as a brown oil 31.68 g, 100%), which was used directly in the following step.

Sodium borohydride (24.97 g, 0.66 mol) and ice/water (400 ml) were stirred with ice/salt bath cooling. The 6-chloronicotinyl chloride (31.68 g, 0.18 mol) was added to the resulting mixture at such a rate as to ensure that, with ice/salt bath cooling, the temperature of the mixture did not rise above 15° C. After addition was complete the temperature of the mixture was allowed to rise to ambient temperature (20° C.) and was stirred at this temperature for 12 hours. The mixture was then extracted with dichloromethane (8×200 ml). The combined extracts were dried (Mg SO$_4$) and evaporated under reduced pressure to give a white solid. The product, 2-chloro-5-hydroxymethyl-pyridine, was isolated from this white solid by flash chromatography using silica gel, 230 to 400 US mesh (0.062 mm to 0.037 mm), with diethylether as eluent, as a white solid (18.76 g, 72.6%).

NMR (CDCl$_3$), delta (ppm): 3.70 (broad, 1H), 4.66 (s,2H), 7.27 (d,1H), 7.65 (d/d, 1H), 8.25 (s,1H).

(b) Preparation of 2-chloro-5-chloromethylpyridine

Thionyl chloride (14.6 ml, 0.2 mol) was added extremely carefully in dropwise manner to a rapidly stirred mixture of 2-chloro-5-hydroxymethylpyridine (18.6 g, 0.13 mol) and chloroform (150 ml) at ambient temperature (20° C.). After addition was complete the resulting mixture was heated under reflux for 12 hours. The reaction mixture was then allowed to cool to ambient temperature (20° C.) and chloroform was evaporated off under reduced pressure to give a brown oil. The product, 2-chloro-5-chloromethyl-pyridine was isolated from this brown oil by flash chromatography using silica gel, 230 to 400 US mesh (0.062 mm to 0.037 mm), with dichloromethane as eluent, as a yellow oil which solidified on standing (17.45 g, 82.9%).

NMR (CDCl$_3$), delta (ppm): 4.55(s,2H), 7.35(d,1H), 7.70 (d/d,1H), 8.40(d,1H).

(c) Preparation of N-(6-chloro-3-pyridylmethyl) phthalimide

2-Chloro-5-chloromethylpyridine (8.1 g, 0.05 mol) and potassium phthalimide (10.2 g, 0.055 mol) were mixed together at ambient temperature (20° C.) and the resulting mixture was then heated with stirring at 160° C. for 12 hours. The reaction mixture was then cooled to ambient temperature (20° C.) and dichloromethane was added until most of the solid residue had dissolved. The dichloromethane extract was then washed with water (2×150 ml) and brine (1×200 ml), dried using magnesium sulphate, and evaporated under reduced pressure to give a light-brown solid. The title product, N-(6-chloro-3-pyridylmethyl) phthalimide, was isolated from this solid by flash chromatography using silica gel, 230 to 400 US mesh (0.062 mm to 0.037 mm), with 10% v/v ether/ dichloromethane as eluent, as a buff solid (10.70 g, 78.5%), mp 140° to 142° C.

NMR (CDCl$_3$, delta (ppm): 4.81 (s,2H), 7.25 (d,1H), 7.72 (m,3H), 7,83 (m,2H), 8.47 (d,1H).

(d) Preparation of 6-chloro-3-pyridylmethylamine

Hydrazine hydrate (2.00 ml, 0.04 mol) was added at ambient temperature (20° C.) to a solution of N-(6-chloro-3-pyridylmethyl) phthalimide (10.70 g, 0.039 mol) in ethanol (150 ml), and the resulting solution was heated under reflux for 4 hours before being cooled to ambient temperature (20° C.). 25% w/v aqueous hydrochloric acid (60 ml) was added directly and the resulting mixture was heated under reflux for 1 hour. The reaction mixture was then cooled to ambient temperature (20° C.), filtered and evaporated under reduced pressure. The resulting concentrated mixture was filtered and the filtrate was cooled, with ice/salt bath cooling, and solid potassium hydroxide was added with stirring until the mixture became basic. The reaction mixture was then extracted with diethylether (5×150 ml). The combined ether extracts were dried using magnesium sulphate and evaporated under reduced pressure to give the product, 6-chloro-3-pyridylmethylamine as a brown oil (5.07 g, 90.6%).

NMR(CDCl$_3$), delta (ppm): 1.48 (broad, 2H), 3.81 (s,2H), 7.21 (d,1H), 7.59 (d/d,1H), 8.24(s,1H).

EXAMPLE 5

N-(6-chloro-3-pyridylmethyl)-N-methylamine

A mixture of the product of Example 4(b), 2-chloro-5-chloromethylpyridine, (8.1 g, 0.05 mol), methylamine (60 ml of a 30% w/v solution in water, 0.5 mol) and ethanol (100 ml) was heated, with stirring, under reflux for 5 hours. The reaction mixture was then cooled to ambient temperature (20° C.) and the solvent removed by evaporation under reduced pressure to give a brown oil. The product, N-(6-chloro-3-pyridylmethyl)-N-methylamine, was isolated from this oil by flash chromatography using silica gel, 230 to 400 US mesh (0.062 mm to 0.037 mm), with 10% v/v methanol/dichloromethane as eluent, as a brown oil (5.96 g, 76.1%).

NMR (CDCl$_3$), delta (ppm):1.36 (broad s,1H), 2.37 (s,3H), 3.67 (s,2H), 7.25 (d,1H), 7.50 (d/d,1H), 8.24 (s,1H).

EXAMPLE 6

1-(6-chloro-3-pyridylmethyl)amino-1-methylthio-4,4,4-trifluoro-1-buten-3-one The product of Example 1, 1, 1-bismethylthio-4,4,4-trifluoro-1-buten-2-one, (4.32 g, 0.02 mol) and the product of Example 4, 6-chloro-3pyridylmethylamine (2.85 g, 0.02 mol) were dissolved in ethanol (50 ml). The resulting solution was heated under reflux for 2 hours under an atmosphere of nitrogen. The resulting mixture was cooled to ambient temperature (20° C.) and the solvent removed by evaporation under reduced pressure. The residue was chromatographically purified using a silica gel column eluted with dichloromethane/ether (19:1) to give the product, 1-(6-chloro-3-pyridylmethyl) amino-1-methylthio-4,4,4-trifluoro-1-buten-3-one, as a solid which recrystallized from ethanol, in a yield of 3.32 g (53%), melting point 112° C.

Analysis: Calculated: 42.5%C 3.2%H 9.0%N
Found : 42.3%C 3.6%H 9.0%N

EXAMPLE 7

1-(6-chloro-3-pyridylmethyl)amino-1-methylamino-4,4,4-trifluoro-1-buten-3-one The product of Example 6, 1-(6-chloro-3-pyridylmethyl) amino-1-methylthio-4,4,4-trifluoro-1-buten-3-one (4.66 g, 0.015 mol) and methylamine (0.53 g, 0.017 mol) were dissolved in ethanol (50 ml). The resulting solution was heated under reflux with stirring for 6 hours. The resulting mixture was allowed to cool to ambient temperature (20° C.) and the solvent was removed by evaporation under reduced pressure. The residue was purified using a silica gel column eluted with dichloromethane/methanol (30:1). The product, 1-(6-chloro-3-pyridylmethyl)-amino-1-methylamino-4, 4,4-trifluoro-1-buten-3-one, was obtained as a white solid which recrystallized from ethanol, in a yield of 2.93 g (66%), melting point 114° C.

Analysis: Calculated: 45.0%C 3.8%H 14.3%N
Found 44.9%C 4.1%H 13.8%N

EXAMPLE 8

1-(6-chloro-3-pyridylmethyl)amino-1-dimethylamino 4,4,4-trifluoro-1-buten-3-one The product of Example 6, 1-(6-chloro-3-pyridylmethyl) amino-1-methylthio-4,4,4-trifluoro-1-buten-3-one, (2.0 g, 0.0065 mol) and dimethylamine (1.5 ml) were dissolved in ethanol (15 ml). The resulting solution was heated under reflux for 2 hours. The resulting mixture was cooled to ambient temperature (20° C.) and solvent removed by evaporation under reduced pressure. The solid residue was recrystallized from ether to give the product, 1-(6-chloro-3-pyridylmethyl)amino-1-dimethylamino-4,4,4-trifluoro-1-buten-3-one, in a yield of 0.3 g (16%), melting point 85° C.

Analysis: Calculated: 46.8%C 4.3%H 13.7%N
Found: 46.9%C 4.3%H 13.6%N

EXAMPLE 9

1-[N-(2-chloro-5-thiazolylmethyl)-N-methyl]amino-1-methylthio-4, 4,4-trifluoro-1-buten-3-one The product of Example 1, 1,1-bismethylthio-4,4,4-trifluoro-1-buten-2-one, (2.1 g, 0.0097 mol) and the product of Example 3, N-(2-chloro-5-thiazolylmethyl)-N-methylamine, (1.4 g, 0.0086 mol) were dissolved in toluene (25 ml). The resulting solution was heated to 90° C. and held at that temperature for 4 hours. The resulting mixture was cooled to ambient temperature (20° C.) and the solvent removed by evaporation at reduced pressure. The residue was purified using a silica gel column eluted with dichloromethane/methanol (30:1).

The product was obtained as a yellow oil in a yield of 1.17 g (41%).
Analysis: Calculated: 36.3%C 3.1%H 8.5%N
Found 35.9%C 2.9%H 8.5%N

EXAMPLE 10

1-[N-(2-chloro-5-thiazolylmethyl)-N-methyl]amino-1-dimethylamino-4, 4,4-trifluoro-1-buten-3-one The product of Example 2, 1-dimethylamino-1-methylthio-4,4,4-trifluoro-1-buten-3-one, (0.64 g, 0.003 mol) and the product of Example 3, N-(2-chloro-5-thiazolylmethyl)-N-methylamine, (0.41 g, 0.0027 mol) were dissolved in ethanol (50 ml). The resulting solution was heated to 50° C. and held at that temperature for 20 hours. The resulting mixture was allowed to cool to ambient temperature (20° C.). The product, 1-[N-(2-chloro-5-thiazolylmethyl)-N-methyl]amino-1-dimethylamino-4,4,4-trifluoro-1-buten-3-one was obtained by chromatographic purification using a silica column eluted with dichloromethane/methanol (30 1) as a yellow oil in a yield of 0.1 g.
NMR (CDCl$_3$), delta (ppm): 2.80 (s,3H), 2.98 (s,6H), 4.56 (s,2H), 4,84 (s,1H), 7.46 (s,1H).

EXAMPLE 11

1-[N-(6-chloro-3-pyridylmethyl)-N-methyl]amino-1-methylthio-4, 4,4-trifluoro-1-buten-3-one The product of Example 1, 1,1-bismethylthio-4,4,4-trifluoro-1-buten-3-one, (2.16 g, 0.01 mol) and the product of example 5, N-(6-chloro-3-pyridylmethyl)-N-methylamine, (1.57 g, 0.01 mol) were dissolved in ethanol (25 ml). The resulting solution was heated to 60° C. and held at that temperature for 4 hours. The resulting mixture was allowed to cool to ambient temperature (20° C.). The product, 1-[N-(6-chloro-3-pyridylmethyl)-N-methyl]amino-1-methylthio-4,4,4-trifluoro-1-buten-3-one was obtained by chromatographic purification on a silica column eluted with dichloromethane/methanol (20:1) as an oil in a yield of 0.88 g (27%).
NMR (CDCl$_3$), delta (ppm):2.51 (s,3H), 3.12 (s,3H), 4.84 (s,2H), 5.37 (s,1H), 7.35 (d,1H), 7.56 (dd,1H), 8.27 (d,1H).

EXAMPLE 12

1-[N-(6-chloro-3-pyridylmethyl)-N-methyl]amino-1-methylamino-4, 4,4-trifluoro-1-buten-3-one Following the general procedure of Example 7, the product 1-[N-(6-chloro-3-pyridylmethyl)-N-methyl]amino-1-methylamino-4,4,4-trifluoro-1-buten-3-one, was prepared using, as starting materials, the product of Example 9, 1-[N-(6-chloro-3-pyridylmethyl)-N-methyl]amino-1-methylthio-4,4,4-trifluoro-1-buten-3-one, (0.45 g) and methylamine (0.05 g), as an oil in a yield of 0.2 g (49%).
NMR (CDCl$_3$), delta (ppm): 2.84 (s,3H), 3.00 (d,3H), 4.43 (s,2H), 5.04 (s,1H), 7.40 (d,1H), 7.54 (dd,1H), 8.30 (d,1H), 10.42 (broad,1H)

EXAMPLE 13

1-[N-(2-chloro-5-thiazolylmethyl)-N-methyl]amino-1-ethylamino-4, 4,4-trifluoro-1-buten-3-one The product of Example 9, 1-[N-(2-chloro-5-thiazolylmethyl)-N-methyl]amino-1-methylthio-4,4,4-trifluoro-1-buten-3-one (0.99 g, 0.003 mol) and ethylamine (0.25 g, 0.005 mol) were dissolved in ethanol (10 ml). The resulting solution was heated under reflux for 2½ hours. The resulting mixture was allowed to cool and the solvent removed yielding an oil. The product, 1-[N-(2-chloro-5-thiazolymethyl)-N-methyl]-amino-1-ethylamino-4, 4,4-trifluoro-1-buten-3-one, was obtained by chromatographic purification of the oil using a silica column eluted with dichloromethane/ methanol (25:1) as a yellow oil in a yield of 0.38 g (39%).
Analysis: Calculated: 40.3% C 4.0% H 12.8% N
Found 40.6% C 4.1% H 12.9% N

EXAMPLE 14

1-[N-(6-chloro-3-pyridylmethyl)-N-trifluoroacetyl]-amino-1-methylamino-4, 4,4-trifluoro-1-buten-3-one The product of example 7, 1-(6-chloro-3-pyridylmethyl)-amino-1-methylamino-4, 4,4-trifluoro-1-buten-3-one (0.62 g, 0.0021 mol) and pyridine (0.2 ml) were dissolved in dry dichloromethane (10 mls) at a temperature of 0° C. Trifluoroacetic anhydride (0.46 g, 0.0022 mole) was added dropwise to the resulting solution over a period of 10 mins. The resulting mixture was allowed to warm to 20° C. and held at this temperature for 2 hrs. The resulting mixture was added to dichloromethane (100 ml) and the resulting mixture was washed with water (3×50 ml) and saturated brine (50 ml), and finally dried using magnesium sulphate. The solvent was then evaporated to yield a gum. The product, 1[N-(6-chloro-3-pyridylmethyl)-N-trifluoroacetyl]amino-1-methylamino-4,4,4-trifluoro-1-buten-3-one was obtained by crystallisation from ether as a white solid in a yield of 0.17 g (21%), melting point 134° C.
Analysis Calculated: 40.1% C 2.6% H 10.8% N
Found: 40.4% C 2.6% H 11.2% N

EXAMPLE 15

Pesticidal Activity

Pesticidal activity of compounds of the invention was assessed against various of the following pests:-
*Spodoptera littoralis* (Egyptian cotton leafworm)
*Aedes aegypti* (yellow fever mosquito)
*Musca domestica* (housefly)
*Acyrthosiphon pisum* (pea aphid)
*Nephotettix cincticeps* (green leaf hopper)
*Nilaparvata lugens* (brown rice plant hopper)
*Plutella xylostella* (diamond-back moth)
*Megoura viciae* (vetch aphid)
*Aphis fabae* (black bean aphid)

The test methods employed for each species appear below. In each test, unless otherwise stated, solutions or suspensions of test compound were made up over a range of concentrations in water (initially 0.1%w) containing 10%w acetone and 0.025%w "TRITON X-100" (trade mark) surface active agent (the condensation product of ethylene oxide with an alkyl phenol). These solutions were sprayed at a rate equivalent to 340 liters per hectare (3.4×10$^{-5}$m$^3$/m$^2$) onto petri dishes containing either test species per se or diet onto which test species were subsequently introduced, as indicated. The tests were all conducted under normal insectary conditions (23° C. ±2° C., fluctuating humidity and light).

The results of testing at the initial test concentrations were graded A, B or C.
Grade A represents at least 70% mortality of the pest,
Grade B represents between 40% and 70% mortality, and
Grade C represents less than 40% mortality.

For compounds achieving Grade A at initial test concentration, mortality assessments were made as indicated below, in terms of percentage mortality figures. In each test a $LC_{50}$ (the dosage of active material required to kill half of the test species) for the compound was calculated from the mortality figures and compared with the corresponding $LC_{50}$ for a standard insecticide (either ethyl parathion or chlorfenson, as indicated) in the same test. The results are expressed as toxicity indices thus:

$$\text{toxicity index} = \frac{LC_{50} \text{ (standard insectide)}}{LC_{50} \text{ (test compound)}} \times 100$$

(i) Spodoptera littoralis (ovicidal) (S1)

Test solutions were sprayed as described above onto Petri dishes containing filter papers on which were approximately fifty 24 hours old eggs. After 6 days the numbers of hatched and unhatched eggs were counted and percentage mortality calculated.

(ii) Aedes aeqypti (Aa)

Test solutions were made up to 0.5 ppm of test compound (and progressive half-dilutions) in water; acetone was initially present to aid solution, but was allowed to evaporate off before introduction of larvae.

Ten early 4th instar larvae were placed in 100 ml of test solution and larval mortality was recorded after 2 days (Aa 2D). A pinch of ground animal feed was introduced and a further assessment of mortality was made after 7 days. (Aa 7D).

(iii) Musca domestica (Md)

Batches of ten 2 to 3 day old milk-fed adult female houseflies, anaesthetised using carbon dioxide, were placed on filter papers inside Petri dishes. The dishes were sprayed with the test solutions as described above. The flies were retained in the Petri dishes and were fed with a dilute milk solution which was dripped down the side of the Petri dish and absorbed by the filter paper. Mortality was assessed after 24 hours.

(iv) Acyrthosiphon pisum (Ap)

Tests were carried out on young adult pea aphids. Whole pea plants 6 days after germination were placed on filter papers in Petri dishes. Ten aphids were transferred to each pea plant and left for 30 minutes to allow the aphids to settle and start to feed. The dishes were then sprayed with the test solutions as described above and lids were placed on the Petri dishes. Mortality was assessed after 24 hours.

(v) Nephotettix cincticeps (Nc)

Tests were carried out on young adult female green leaf hoppers. Plant pots, each containing five rice seedlings 10 to 15 cm tall arranged across the centre of the pot, were sprayed with test solutions as described above (but initial test concentration 0.05% of the test compound). Spraying was on both sides of the plants with the pots horizontal. One hour after spraying, each pot was filled to the brim with fine silver sand, an open-ended glass jar was placed over each pot and each pot was infested with ten hoppers. A paper tissue was placed over the open end of each glass jar to retain the hoppers. The pots were irrigated from underneath, maintained at a temperature of 27° C.±2° C. and subjected to white fluorescent light under a regime of 18 hours light followed by 6 hours darkness. Mortality assessments were made 48 hours after infestation.

(vi) Nilaparvata luqens (Nl)

Tests were carried out on young adult female brown rice plant hoppers in the same way as for green leaf hoppers in (v) below.

(vii) Plutella xylostella (Px)

Test solutions were sprayed as described above onto Petri dishes containing 9 cm discs of Chinese cabbage leaves on filter papers. After drying, each dish was infested with ten 3rd instar diamond-back moth larvae. Mortality assessments were made 24 hours after infestation.

(viii) Megoura viciae (Mv)

Tests were carried out on adult vetch aphids. Pairs of broad bean leaves on filter paper in Petri dishes were sprayed side by side with uncounted quantities of aphids in small gauze-covered containers. After passing through the spray aphids were tipped onto the leaves and lids were placed on the Petri dishes. Mortality was assessed after 24 hours.

(ix) Aphis fabae (Af)

Tests were carried out on adult black bean aphids. Pairs of broad been leaves on filter paper in Petri dishes were sprayed side by side with uncounted quantities of aphids in small gauze-covered containers. After passing through the spray aphids were tipped onto the leaves and lids were placed on the Petri dishes. Mortality was assessed after 24 hours.

Results of the above tests, only some of which were performed on each compound, are given in Table I following:

TABLE 1

| Compound of Example | Toxicity Indices (compared with ethyl parathion, except * compared with chlorfenson) | | | | | | | | | |
|---|---|---|---|---|---|---|---|---|---|---|
| | S1* | Aa 2D | Aa 7D | Md | Ap | Nc | Nl | Px | Mv | AF |
| 6 | | | | | | <10 | | | | |
| 7 | 7 | B | <1 | 1 | 11 | 170 | <35 | <10 | 300 | 80 |
| 8 | | | | <1 | 12 | 740 | <140 | | | |
| 10 | | | | | A | | | | | |
| 11 | | | | | 1 | | | | | |
| 12 | | | B | B | 12 | 20 | | | | |
| 13 | | | <2 | | | | | | | |
| 14 | | <1 | <1 | A | A | A | | | | |
| Comparative A | C | C | C | C | C | C | | | | |
| Comparative B | C | C | C | C | C | C | | | | |

"Comparative A" is the compound 1-(3-pyridylmethyl) amino-1-dimethylamino-4,4,4-trifluoro-1-buten-3-one, yellow oil, which was prepared in analogous manner to Example 8.

"Comparative B" is the compound 1-(3-pyridylmethyl) amino-1-methylthio-4,4,4-trifluoro-1-buten-3-one, melting point 89° C., which was prepared in analogous manner to Example 6.

The data set out in Table 1 clearly indicated that the exemplified compounds of the present invention exhibit a much greater level of insecticidal activity than either of the comparative compounds A and B.

EXAMPLE 16

Thermal Stability

The thermal stability of compounds of the present invention was assessed and compared with "Comparative C", the compound 1-(6-chloro-3-pyridylmethyl) amino-1-methylamino-2-nitroethylene specifically described and exemplified as compound 28, Example 10, in the specification of EP-A-0 302 389, using the following test procedure:

Test compound (20 mg) was placed into a platinum crucible. The crucible was loaded into a Stanton Redcroft STA780 thermal analyser and heated from 30° C. to 500° C. in a static atmosphere of air at a temperature increase rate of 3° C. per minute. Thermal changes in the test compound were monitored and the temperature at which the test compound decomposed was recorded.

The results of the tests are set out in Table 2 below:

TABLE 2

| Compound of Example | Temperature of decomposition (°C.) |
|---|---|
| 7 | >400 |
| Comparative C | 186* |

*exothermic decomposition

EXAMPLE 17

Photo Stability

The photo stability of compounds of the present invention was assessed and compared with "Comparative C", the compound 1-(6-chloro-3-pyridylmethyl)amino-1-methylamino-2-nitroethylene specifically described and exemplified as compound 28, Example 10, in the specification of EP-A-0 302 389, using the following test procedure:

The test compound was dissolved in acetonitrile and the resulting solution mixed with water and buffered to pH7 to give a concentration of 7 ppm test compound. The resulting test mixture was placed in a stoppered quartz tube (volume 10 cm$^3$, surface area 30 cm$^3$). The tube was loaded into a Hanau solar simulator light cabinet having a spectral output equivalent to that of natural sunlight. A sample of the test mixture was analysed after a period of about 25 hours exposure, from which the photolytic half life (t½), that is the period of exposure required to decompose half the test compound present at the start of the test, was calculated.

The results of the tests are set out in Table 3 below:

TABLE 3

| Compound of Example | t½ (hours) |
|---|---|
| 7 | 105 |
| 8 | 55 |
| Comparative C | 0.5 |

We claim:

1. A butenone compound having the formula I:

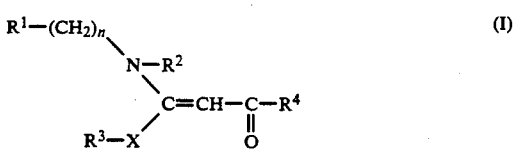

wherein R$^1$ is 6-chloro-3-pyridyl;
R$^2$ represents a hydrogen atom, an alkyl group or an halosubstituted alkylcarbonyl group;
R$^3$ represents an alkyl group;
R$^4$ represents a trifluoromethyl group;
X represents a sulphur atom; and
n is 0 or 1.

2. A compound selected from the group consisting of 1-(6-chloro-3-pyridylmethyl)amino-1-methylamino-4,4,4-trifluoro-1-buten-3-one and 1-(6-chloro-3-pyridylmethyl) amino-1-dimethylamino-4,4,4-trifluoro-1-buten-3-one.

3. The compound of claim 2 wherein said compound is 1-(6-chloro-3-pyridylmethyl)amino-1-dimethylamino-4,4,4-trifluoro-1-buten-3-one.

4. A compound according to claim 1, defined as 1-(6-chloro-3-pyridylmethyl) amino-1-alkylthio-4,4,4-trifluoro-1-buten-3-one.

5. A compound according to claim 4, wherein said alkylthio is methylthio.

6. A compound according to claim 1, defined as 1-[N-(6-chloro-3-pyridylmethyl)-N-trifluoroacetyl]amino-1-alkylamino-4,4,4-trifluoro-1-buten-3-one.

7. A compound according to claim 6, wherein said alkylamino is methylamino.

8. A pesticidal composition comprising an effective amount of the compound of claim 2.

9. A pesticidal composition comprising an effective amount of the compound of claim 4.

10. A pesticidal composition comprising an effective amount of the compound of claim 6.

11. A method of combatting pests at a locus, which method comprises treating the locus with an effective amount of the compound as claimed in claim 2.

12. A method of combatting pests at a locus, which method comprises treating the locus with an effective amount of the compound as claimed in claim 4.

13. A method of combatting pests at a locus, which method comprises treating the locus with an effective amount of the compound as claimed in claim 6.

* * * * *

UNITED STATES PATENT AND TRADEMARK OFFICE
CERTIFICATE OF CORRECTION

PATENT NO. : 5,225,423
DATED : July 6, 1993
INVENTOR(S) : ANTONIO METE ET AL.

It is certified that error appears in the above-identified patent and that said Letters Patent is hereby corrected as shown below:

Column 18,
Claim 4, which reads as follows: "4. A compound according to claim 1, defined as 1-(6-chloro-3-pyridylmethyl)amino-1-alkylthio-4,4,4-trifluoro-1-buten-3-one." should read --4. The compound 1-(6-chloro-3-pyridylmethyl)amino-1-alkylthio-4,4,4-trifluoro-1-buten-3-one.--

Column 18,
Claim 6, which reads as follows: "6. A compound according to claim 1, defined as 1-[N-(6-chloro-3-pyridylmethyl)-N-trifluoroacetyl]amino-1-alkylamino-4,4,4-trifluoro-1-buten-3-one." should read --6. The compound 1-[N-(6-chloro-3-pyridylmethyl)-N-trifluoroacetyl]amino-1-alkylamino-4,4,4-trifluoro-1-buten-3-one.--

Signed and Sealed this

Twenty-eight Day of March, 1995

Attest:

BRUCE LEHMAN

*Attesting Officer*   *Commissioner of Patents and Trademarks*